(12) United States Patent
Sichtermann et al.

(10) Patent No.: US 10,413,669 B2
(45) Date of Patent: Sep. 17, 2019

(54) DISPOSABLE INJECTOR HAVING A SOUND-PROOFING LAYER

(71) Applicant: LTS LOHMANN THERAPIE-SYSTEME AG, Andernach (DE)

(72) Inventors: Thorsten Sichtermann, Neustadt-Wied (DE); Uwe Wortmann, Marburg (DE)

(73) Assignee: LTS LOHMANN THERAPIES-SYSTEME AG, Andernach (DE)

( * ) Notice: Subject to any disclaimer, the term of this patent is extended or adjusted under 35 U.S.C. 154(b) by 19 days.

(21) Appl. No.: 15/721,997

(22) Filed: Oct. 2, 2017

(65) Prior Publication Data

US 2018/0021516 A1    Jan. 25, 2018

Related U.S. Application Data

(63) Continuation-in-part of application No. PCT/EP2015/059693, filed on May 4, 2015.

(51) Int. Cl.
*A61M 5/20* (2006.01)
*A61M 5/31* (2006.01)

(52) U.S. Cl.
CPC ... *A61M 5/2033* (2013.01); *A61M 2005/2073* (2013.01); *A61M 2005/2086* (2013.01); *A61M 2005/312* (2013.01); *A61M 2005/3143* (2013.01); *A61M 2205/02* (2013.01)

(58) Field of Classification Search
CPC ........ A61M 2005/2086; A61M 5/2044; A61M 2005/312; A61M 2005/2073
See application file for complete search history.

(56) References Cited

U.S. PATENT DOCUMENTS

| 6,004,286 | A | 12/1999 | Bellhouse et al. | |
|---|---|---|---|---|
| 8,591,463 | B1* | 11/2013 | Cowe | A61M 5/20 604/117 |
| 2003/0105430 | A1 | 6/2003 | Lavi et al. | |
| 2004/0254525 | A1* | 12/2004 | Uber, III | A61M 5/007 604/67 |
| 2008/0195956 | A1 | 8/2008 | Bishop et al. | |
| 2010/0076373 | A1 | 3/2010 | Matusch | |
| 2010/0076379 | A1 | 3/2010 | Matusch | |
| 2011/0251550 | A1* | 10/2011 | Matusch | A61M 5/30 604/68 |

FOREIGN PATENT DOCUMENTS

WO   WO 2007/138319 A1   12/2007
WO            2506918 A    4/2014

* cited by examiner

*Primary Examiner* — Nathan R Price
*Assistant Examiner* — Melissa A Snyder
(74) *Attorney, Agent, or Firm* — Ronald S. Lombard (57) ABSTRACT

A disposable injector comprising a housing, a spring-loaded piston-actuating plunger arranged in the housing and able to be released by a trigger unit. A cylinder-piston unit comprising a cylinder and a piston that is positioned at a distance from the piston-actuating plunger. A closed layer made on an elastically-deformable material surrounds the piston-actuating plunger in at least some sections and projects beyond same in the trigger direction, resulting in a disposable injector that will not alarm a patient during use thereof.

12 Claims, 7 Drawing Sheets

DISPOSABLE INJECTOR HAVING A SOUND-PROOFING LAYER

CROSS-REFERENCE TO RELATED APPLICATION

This is a continuation-in-part application of pending international application PCT/EP2015/059693 filed May 4, 2015. The said International application PCT/EP2015/059693 is incorporated herein by reference in its entirety as though fully set forth.

BACKGROUND OF THE INVENTION

The invention relates to a single-use injector having a housing, having a resiliently loaded piston actuation ram which is arranged in the housing and which can be unlocked by means of a trigger unit, and having a cylinder/piston unit which comprises a cylinder and a piston which is spaced apart from the piston actuation ram.

DE 10 2007 031 714 A1 discloses such a single-use injector. The triggering of the single-use injector may frighten the patient. The patient may recoil. The single-use injector may thereby slip away from the provided injection location.

The present invention addresses the problem of constructing a single-use injector in such a manner that the patient does not become frightened during use.

SUMMARY OF THE INVENTION

This problem is solved with the features of the claims. To this end, a closed layer of a resiliently deformable material surrounds the piston actuation ram at least partially and protrudes therebeyond in the triggering direction.

Further details of the invention will be appreciated from the claims and the following descriptions of schematically illustrated embodiments.

DETAILED DESCRIPTION OF THE INVENTION

FIGS. 1-7 shows a single-use or disposable injector (4). Such injectors (4) are used for the one-off introduction of an injection solution (1) or a solvent which is stored in a cylinder/piston unit (100) into the skin of a patient.

Figure 1:
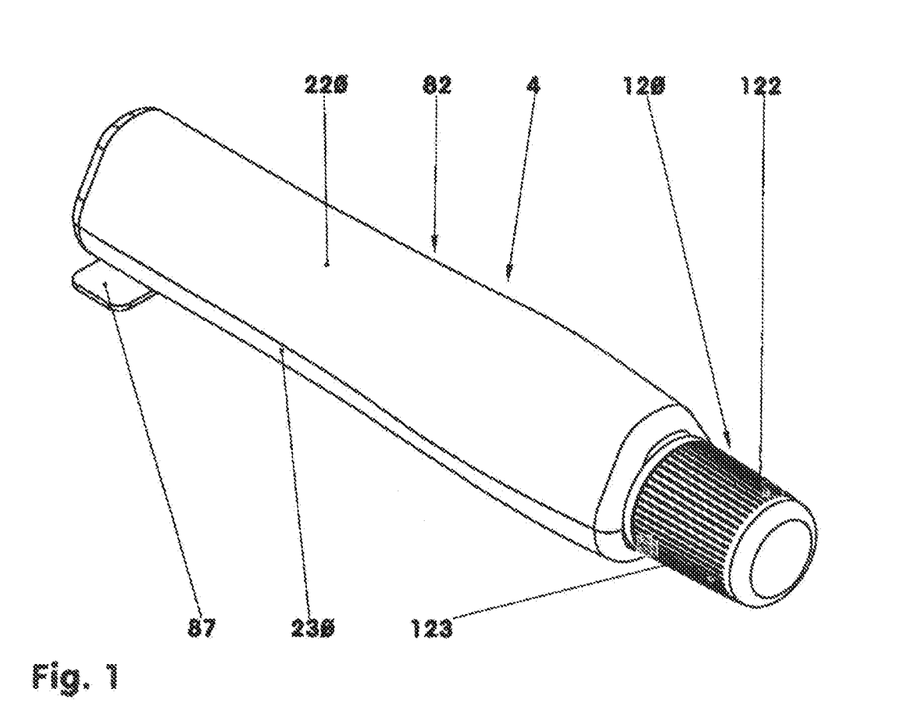
FIG. 1: shows a single-use injector with closure cap.

FIG. 1 is a dimetric view of the single-use injector (4). It has a trigger unit (80) with a two-part triggering sleeve (82) which comprises an upper shell (220) and a lower shell (230) here. This triggering sleeve (82) which is polygonal in cross-section has an at least substantially regular, triangle-like cross-section, cf. FIG. 5. The crosssectional surface-area in the rear region of the disposable injector (4) facing away from the injection location is 70% of the cross-sectional surface-area in the front region of the disposable injector (4) facing the injection location. The constant increase of the cross-sectional surface-area is located, when viewed from the rear, in the third quarter of the length of the disposable injector (4).

The triggering of the single-use injector (4) is prevented by means of a sliding securing member (87). It may be removable for releasing or it may be displaceable in a state guided in the single-use injector (4). The cylinder/piston unit (100) has an outlet opening (106) at the front end thereof.

Figure 2:
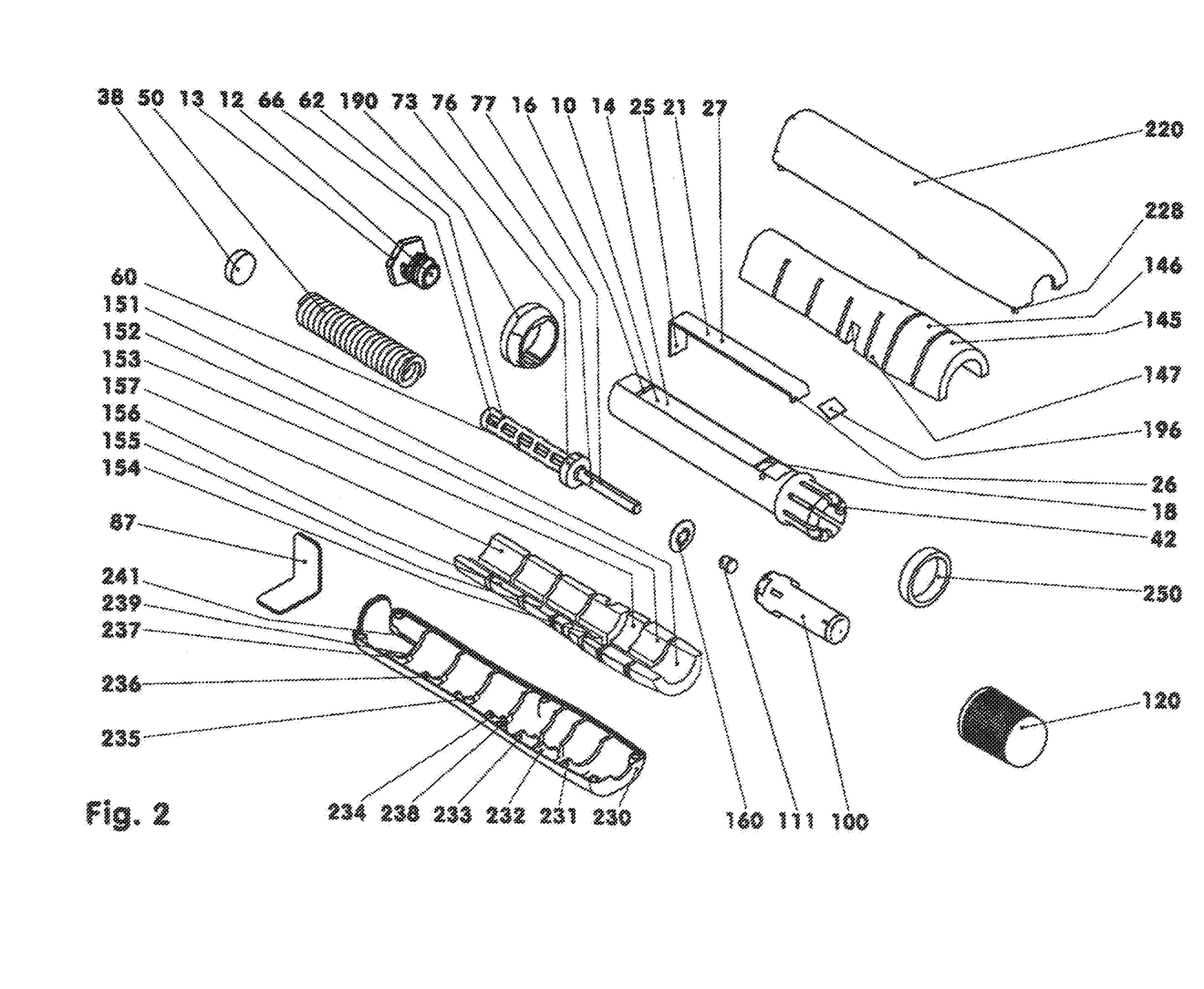
FIG. 2: is an exploded drawing of the single-use injector from FIG. 1.
Figure 3:
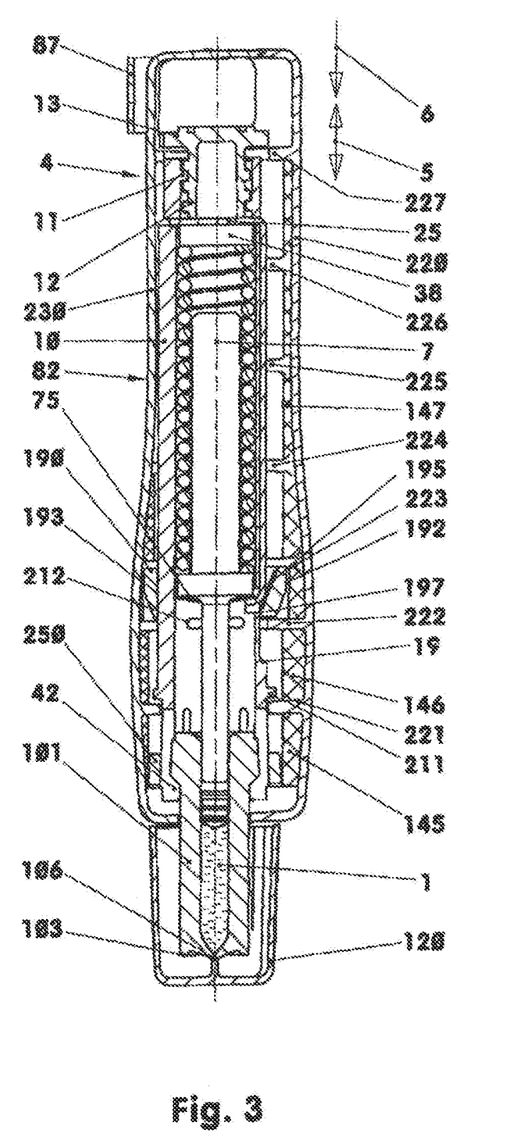
FIG. 3: is a longitudinal section of the single-use injector from FIG. 1.
Figure 4:
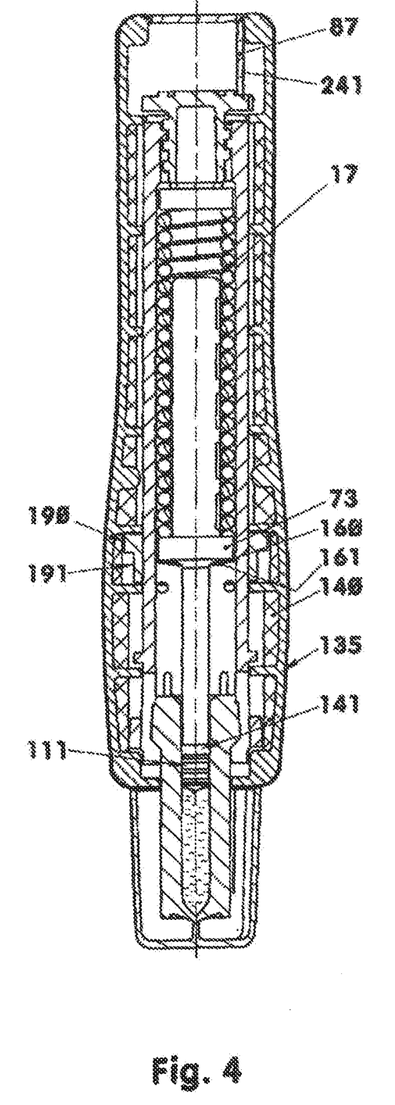
FIG. 4: is a longitudinal section which is normal with respect to FIG. 3.
Figure 5:
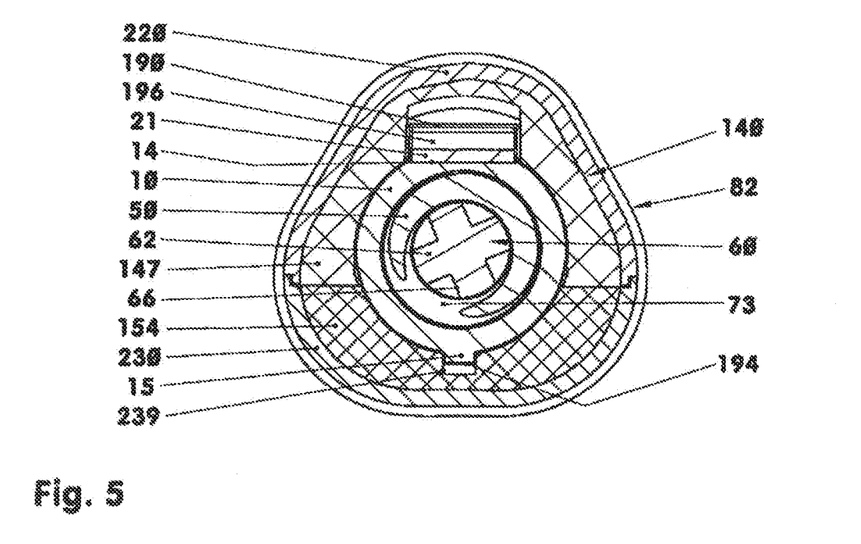
FIG. 5: is a cross-section of the single-use injector above the triggering ring.

FIG. 2 is an exploded view and FIGS. 3 and 4 are longitudinal sections of the non-actuated single-use injector (4). The upper end of the disposable injector (4) in FIGS. 3 and 4 corresponds to the rear end in the illustration of FIG. 1. The disposable injector (4) comprises a tubular housing (10) in which a resilient energy store (50) and a piston actuation ram (60) are arranged. In the front region, the housing (10) has inwardly protruding resilient hooks (42). In the illustrations of FIGS. 3 and 4, the, for example, pre-filled cylinder/piston unit (100) is inserted and engaged in the resilient hooks (42).

The housing (10) has a substantially cylindrical inner contour. An inner thread (11) is arranged in the rear region. A support screw (12) having a hexagonal portion (13) is located therein. The outer contour of the housing (10) has a cylindrical basic shape with a flattened portion (14). In the region of the flattened portion (14), a support rod (21) is in abutment with the housing (10). The opposite side of the housing (10) has a guiding rib (15) which is orientated in the longitudinal direction (5) of the singe-use injector (4).

The piston actuation ram (60) has a cylindrical guiding journal (62), a ram plate (73) and a piston sliding member (76). The guiding journal (62) carries and guides the resilient energy store (50), which is constructed in this instance as a helical compression spring (50). The upper end of the helical compression spring (50) in FIGS. 3 and 4 is supported by means of a disk (38) and a clamping member (25) of the support rod (21) on the support screw (12). The guiding journal (62) has circle-segment-like recesses (66) which are orientated in a radial direction.

The ram plate (73) of the piston actuation ram (60) is constructed in a disk-like manner and orientated normally with respect to the longitudinal center axis (7) of the disposable injector (4). It has a collar face (75) which faces away from the helical compression spring (50) and which is constructed in a conical manner. The apex angle of the notional cone of the collar face (75) is, for example, 160 degrees. A support disk (160) is in abutment with this collar face (75). The support disk (160) is a perforated disk with a wedge-like hub profile. It is constructed in a frustoconical manner as a side view. The support disk (160) is, for example, produced from a metal material, for example, an austenitic steel. In the illustration of FIG. 3, it is fixed in its position by means of a wrap-around hook (26) of the support rod (21).

The rod-like piston sliding member (76) has in the embodiment an at least substantially cylindrical structure. In order to position an assembly tool, it has key flats (77) which are orientated in the longitudinal direction of the single-use injector (4).

The, for example, single support rod (21) is constructed in the form of a strip in the embodiment. It is, for example, produced from an austenitic spring steel. Over the length thereof, it has a, for example, constant, rectangular cross-section. Both ends thereof are bent inward. The upper end in FIG. 3 forms the clamping member (25) which defines with the main member (27) which is orientated in the longitudinal direction an angle of, for example, 90 degrees. The lower end of the support rod (21) in FIG. 3 forms the wrap-around hook (26). It defines with the main member (27) an angle which is greater than a right angle by the inclination angle of the collar face (75) with respect to a normal plane of the longitudinal center axis (7) of the single-use injector (4). The length of the wraparound hook (26) is, for example, 20% of the length of the clamping member (25). In the assembled state, the clamping member (25) protrudes through an upper slotlike housing opening (16) into the inner space (17) of the housing (10). The wrap-around hook (26) protrudes through a lower housing opening (18) with a rectangular cross-section into the housing (10). It is also conceivable to use a plurality of support rods (21). These may be connected to each other in the region of the clamping member (25).

The cylinder/piston unit (100) comprises a, for example, trans-parent cylinder (101) in which, according to the illustration of FIG. 3, a piston (111) is located in the rear position. In the illustration of FIG. 3, the piston (111) is spaced apart from the piston actuation ram (60) by an intermediate space (141). The length of the intermediate space (141) in the longitudinal direction (5) of the single-use injector (4) is, for example, a few millimeters, for example, the spacing is less than ten millimeters.

The lower end of the cylinder (101) in FIGS. 3 and 4 has an outlet opening (106) which is constructed in this instance as a short, cylindrical, nozzle-like hole (106). This outlet opening (106) is closed before the use of the single-use injector (4), for example, by means of a closure cap (120). On the peripheral face (122) thereof, it has a fluting (123) in order to prevent fingers from sliding off.

In the illustration of FIG. 3, when the cylinder/piston unit (100) is assembled, a securing ring (250) is located on the resilient hook (42). The securing ring (250) has in the embodiment a circular base face. The outer diameter thereof is smaller than the inner diameter of the triggering element (82) and smaller than the outer diameter of the closure cap (120).

A triggering ring (190) is located on the housing (10). The covering face thereof has an upper cylindrical portion (192) and a lower portion (191). The lower portion (191) is constructed to be partially cylindrical and partially frusto-conical. The inner wall (193) which is cylindrical in terms of the basic shape has at one side a rotation prevention groove (194) which is orientated in the axial direction (5). At the opposite side, an oblique abutment face (195) is formed. This abutment face (195) is, for example, orientated at an angle of 20 degrees with respect to the longitudinal direction (5) of the single-use injector (4). This angle may be between 10 degrees and 45 degrees. The abutment face (195) terminates at a lower shoulder (197). In the region of this lower shoulder (197), the inner wall is delimited by a chord of the basic shape.

A metal insertion sheet (196) which is constructed as a sliding plate (196) is located on the abutment face (195). The sliding plate (196) is positioned on the shoulder (197). Before the single-use injector (4) is triggered, cf. FIG. 3, the support rod (21) is supported on the sliding plate (196).

The two shells (220, 230) of the triggering sleeve (82) have at the inner side thereof in each case reinforcement ribs (221-227; 231-237). These transverse ribs (221-227; 231-237) are orientated normally with respect to the longitudinal direction (5) of the single-use injector (4). In this instance, the rear reinforcement ribs (223-227; 232-237) each have two portions, between which a groove (239) is arranged. The foremost reinforcement ribs (221, 222; 231) are each constructed in an interruption-free manner. The upper shell (220) and the lower shell (230) are connected to each other by means of a plurality of journal connections (228, 238). In this instance, in the embodiment the upper shell (220) has at the separation joint six journals (228) which engage in journal holes (238) of the lower shell (230). Where applicable, the journal connections (228, 238) may engage with each other during the assembly. Adhesive bonding of the lower shell (230) to the upper shell (220) is also conceivable.

A layer (140) of a resiliently deformable material is arranged in the triggering sleeve (82). The triggering sleeve (82) forms in this instance the carrying region (135) for this layer (140) which may comprise, for example, bitumen, foam, sponge rubber or felt. The elasticity modulus of this material is less than half of the elasticity modulus of the material of the component of the single-use injector (4) which has the carrying region (135). For example, the layer (140) is adhesively bonded, engaged or fixed in its position at that location by means of connection elements. The layer (140) may be connected to the component which carries it by means of a chemical or physical connection. In the assembled state of the disposable injector (4), the layer (140) is constructed peripherally in a radial direction, at least in the region of the front end of the piston actuation ram (60). In the triggering direction (6), the layer (140) protrudes beyond the front end of the piston actuation ram (60). The thickness of the layer (140) corresponds to at least the thickness of the carrier component (135). It may, for example, correspond to up to ten times the thickness of the carrier component (135).

In the longitudinal direction (5) of the single-use injector (4), the layer (140) is sub-divided into individual portions (145-147, 151-157) by the transverse ribs (221-227, 231-237) of the triggering element (82). The portion (153; 147) which is arranged between the second transverse rib (222; 232) and the third transverse rib (223; 233) has a, for example, 15% larger inner diameter than the remaining portions (145, 146; 151, 152, 154-157) of the layer (140).

During assembly of the single-use injector (4), for example, the support disk (160) is first pushed onto the piston sliding member (76) of the piston actuation ram (60). The helical spring (50) is placed on the guiding journal (62) of the piston actuation ram (60). After the clamping member (25) of the support rod (21) has been introduced into the upper housing slot (16), the disk (38) is inserted into the housing (10) from below. Afterwards, the preassembled components (50, 60, 160) are also introduced from below into the housing (10) so that the helical compression spring (50) is in abutment with the disk (38) and it contacts the clamping member (25). The triggering ring (190), in a state guided on the flattened portion (14) and on the guiding rib (15), is pushed from the rear onto the housing (10) until it is located below the rectangular recess (18). For example, the sliding plate (196) may already be inserted in the triggering ring (19) and fixed. An annular housing expansion (19) prevents further movement of the triggering ring (190).

The support screw (12) can now be screwed in until it is in abutment with the clamping member (25) or presses against it. The piston actuation ram (60) is pressed in. In this instance, the helical compression spring (50) is tensioned. For example, the housing (10) is retained in this instance on a retention ring (211). The wrap-around hook (26) of the support rod (21) is introduced into the rectangular recess (18) and placed at the lower side (161) of the support disk (160). The triggering ring (190) is pulled upward until it is in abutment with the support rod (21). The support pod (21) is now supported on the sliding plate (196). In order to secure the assembly position, a, for example, U-shaped curved member may be introduced into assembly openings (212) of the housing (10). This curved member fixes the position of the triggering ring (190) after the clamping device of the resilient energy store (50) has been removed.

In the lower region of the single-use injector (4), the securing ring (250) is pushed onto the resilient hook (42) until it is, for example, in abutment with the retention ring (211). Now, for example, the pre-filled cylinder/piston unit (100) can be inserted into the housing (10) and engaged therein. The securing ring (250) is pulled forward and thus fixes the position of the cylinder/piston unit (100).

The shell-like portions (145-147) of the layer (140) of resiliently deformable material are inserted and fixed in the upper shell (220). The portions (151-157) of the layer (140) are inserted and fixed in the lower shell (230). In this instance, both in the lower shell (230) and in the upper shell (220), the material protrudes slightly beyond the separation plane between the upper shell (220) and the lower shell (230).

The preassembly group with the housing (10) and the cylinder/piston unit {100) is, for example, inserted in the lower shell (230). In this instance, the rib (15) of the housing (10) is centered in the longitudinal groove (239) of the lower shell (230). The triggering ring (190) is located between the transverse ribs (222, 223; 232, 233). The head of the support screw (12) protrudes beyond the rearmost transverse rib (227; 237). The closure cap (120) is outside the triggering sleeve (82). After the securing element (87) has been inserted into the slot (241) of the lower shell (230), it is clamped, for example, between the support screw (12) and the sleeve (82). Where applicable, an additional compression spring between the support screw (12) and the sleeve (82) may increase the resistance against unintentional triggering. The U-shaped curved member can be removed.

At the end of the assembly, the upper shell (220) is placed on the lower shell (230) and secured, for example, by means of adhesive bonding, engagement, etcetera. Now an additional originality closure (90), for example, a banderole, may be fitted over the triggering sleeve (82) and the closure cap (120).

It is also conceivable to carry out the assembly in a different sequence from the one described.

Before the single-use injector (4) is used, the originality closure (90) is first removed. After the closure cap (120) has been removed, the securing element (87) can be pulled out. The single-use injector (4) is now ready for use and is, for example, placed on the skin of the patient. For example, the end face (103) of the cylinder/piston unit (100) bonds to the skin of the patient.

Figure 6:
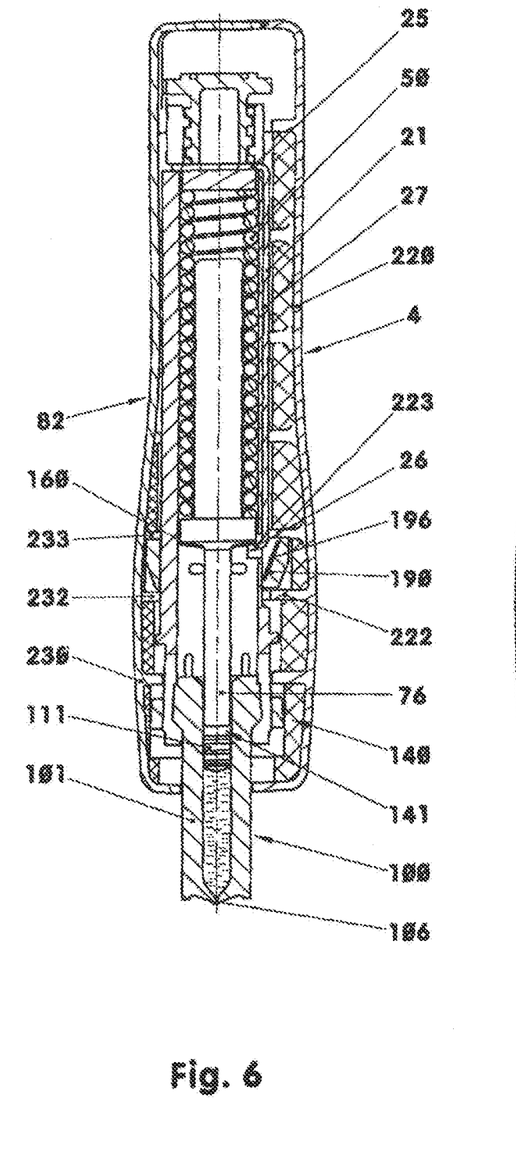
FIG. 6: shows a single-use injector after the triggering.
Figure 7:
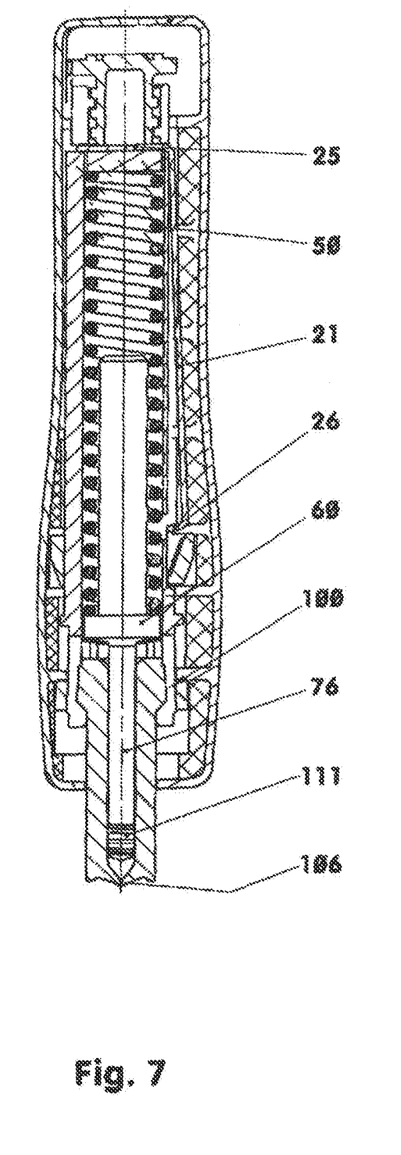
FIG. 7: shows a single-use injector with an emptied cylinder/piston unit.

In order to trigger the single-use injector (4), the triggering sleeve (82) is displaced forward, that is to say, in the direction of the skin of the patient. The triggering sleeve (82) displaces in this instance the triggering ring (190) relative to the housing (10) in a downward direction in the sectioned illustrations of FIGS. 3, 4, 6 and 7. This non-static state is illustrated in FIG. 6. The resilient energy store (50) presses the ram plate (73) forward. In this instance, the pressure disk (160) displaces the wraparound hook (26) of the support rod (21). The support rod (21) slides outward along the sliding plate (196) and consequently completely releases the piston actuation ram (60). The piston actuation ram (60), in a state loaded by the resilient energy store (50) which is becoming relaxed, moves rapidly forward or downward. The piston sliding member (76) strikes the piston (111) and pushes it forward. The injection solution (1) which is stored in the cylinder (101) is displaced through the outlet opening (106) and the hard skin of the patient into the body of the patient. FIG. 7 shows the single-use injector (4) after the triggering.

The noise which occurs when the piston actuation ram (60) strikes the piston (111) spreads both as structure-borne noise and airborne noise in all directions. It strikes in this instance the layer (140) of resiliently deformable material. This material damps the spreading of the noise so that neither the operator nor the patient becomes frightened by the impact and moves the single-use injector (4). During the injection, the complete introduction of the injection solution into the body of the patient is thereby ensured.

The noise insulation layer (140) illustrated in FIGS. 1-7 also surrounds the region of the support rod (21) and the resilient energy store, (50) at least in a radial direction. The spreading of the noise which occurs when the wrap-around hock (26) is released and when the helical compression spring (50) shoots forward is also thereby prevented. Where applicable, the support rod (21) may strike a rubber layer. The operator and the patient are consequently not irritated by the triggering of the disposable injector (4).

Figure 8:
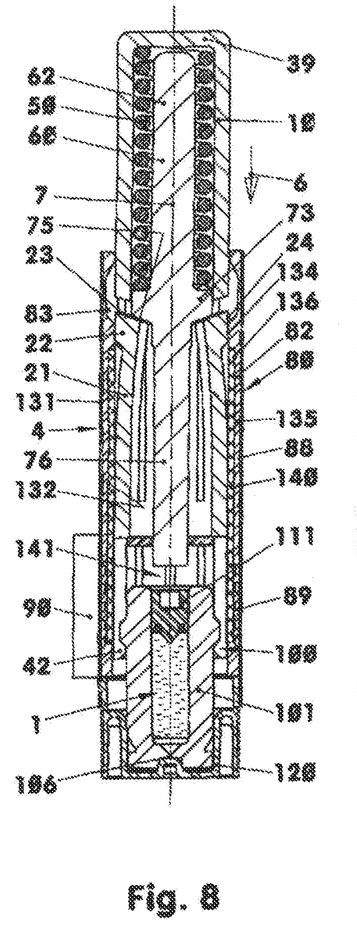
FIG. 8: is a sectioned view of a single-use injector with an inserted cylinder/piston unit.
Figure 9:
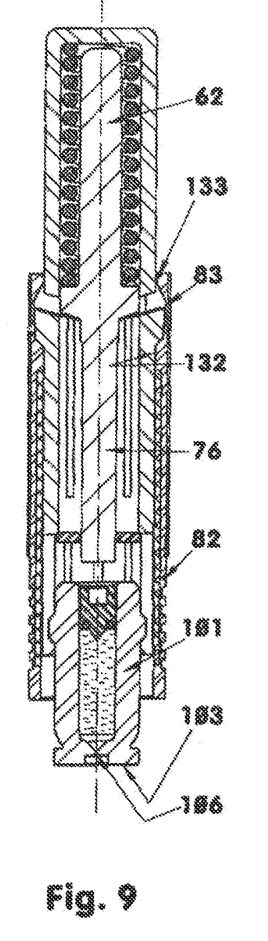
FIG. 9: shows a single-use injector after the triggering.
Figure 10:
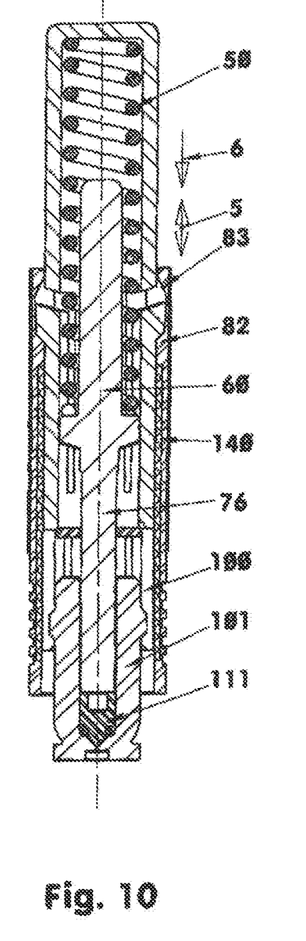
FIG. 10: shows a single-use injector with an emptied cylinder/piston unit.

FIGS. 8 to 10 show another construction type of a single-use or disposable injector (4). In FIG. 8, the single-use injector (4) is illustrated after the insertion of the cylinder/piston unit (100). FIG. 9 shows the non-static state when the single-use injector (4) is triggered. In FIG. 10, the single-use injector (4) is illustrated after use, that is to say, after the solution (1) has been dispensed.

The single-use injector (4) of this embodiment comprises a housing (10) which is constructed in a pot-like manner with an upper base (39). The resilient energy store (50), for example, a helical compression spring (50) which is supported on the base (39) of the housing (10), is arranged in the housing (10). The helical compression spring (50) acts on the piston actuation ram (60). It also guides in this embodiment by means of the, for example, cylindrical guiding journal (62) the lower end of the helical compression spring (50) in FIG. 8.

The piston actuation ram (60) further comprises the ram plate (73) and the, for example, cylindrical piston sliding member (76). The ram plate (73) has a conical collar face (75). By means of this collar face (75), the piston actuation ram (60) is supported on resiliently deformable support rods (21) of the housing (10). It is also conceivable to use only one support rod.

The support rods (21) are in this embodiment flexible, freely protruding rods whose lower end is connected, for example, to the housing (10). At the upper end thereof, they have outwardly protruding cams (22). These have an upper support face (23) on which the ram plate (73) is positioned. The outwardly facing face (24) is an abutment face (24). In the illustration of FIG. 8, the lower end of the piston sliding member (76) is the lower end of the piston sliding member located a few millimeters above the cylinder/piston unit (100).

In the lower region, the housing (10) illustrated in FIGS. 8-10 also has inwardly protruding resilient hooks (42) in which the, for example, pre-filled cylinder/piston unit (100) is inserted and engaged. In the illustration of FIGS. 8 and 9, the piston (111) is located in the rear position thereof. The piston actuation ram (60) and the piston (111) are spaced apart from each other by an intermediate space (141). The upper end of the piston (111) may also be located above or below the upper edge plane of the cylinder (101). The outlet opening (106) which is sealed prior to the use of the single-use injector (4) is constructed as described in connection with the first embodiment.

The single-use injector (4) further comprises a triggering unit (80). This comprises in the embodiment a tubular triggering element (82). The outer wall (88) of the triggering element (82) has, for example, gripping webs (89) which extend in the lower region. In the upper region, the triggering element (82) is reinforced by means of longitudinal ribs (131).

The inner wall (132) of the triggering element (82) has in the upper region an expansion (83) and a peripheral inner ring (133) which is located thereabove. In the assembled state illustrated in FIG. 8, this expansion (83) is located above the support rods (21). Below the expansion (83), the cams (22) are in abutment with the abutment faces (24) thereof against a cylindrical portion (134) of the inner wall (132). The region (135) which adjoins below is constructed in the embodiment as a peripheral carrying region (135). In the illustrations of FIGS. 8 to 10, the inner wall (132) of the triggering element (82) is recessed. A peripheral layer (140) of a resiliently deformable material is arranged in this carrying region (135). The structure of the layer (140) corresponds to the structure of the layer (140) which is mentioned in connection with the first embodiment.

It is also conceivable to secure the layer (140) only in a part-region of the illustrated recess (136). The layer (140) may then, for example, be constructed in a self-supporting manner. The inner wall (135) of the triggering element (82) may be constructed below the expansion (83) in a cylindrical manner without any recess (136). The carrying region (135) is also in this instance the inner wall (132) of the triggering element (82), to which the layer material (140) is secured.

Below the triggering element (82) a closure cap (120) is illustrated in the illustration of FIG. 8. This is, for example, engaged with the housing (10) and closes the outlet opening (106) of the cylinder/piston unit (100). In the delivery state, the disposable injector (4) is additionally wrapped with a banderole (90) which forms an originality closure (90).

The housing (10), the triggering element (82), the piston actuation ram (60) of the cylinders, the piston (111) and the closure cap (120) are, for example, produced from plastics materials. These may be shock resistant thermosetting plastics materials or thermoplastics. The components mentioned may have normally with respect to the longitudinal direction (5) thereof an annular, circular, square, hexagonal, etcetera, solid or tubular cross-sectional surface area.

During the assembly, the piston actuation ram (60) is inserted together with the spring (50) into the housing (10) and the triggering element (82) is pushed thereover. The support rods (21) which are in abutment with the triggering element (82) and which support the ram plate (73) thereby retain the resilient energy store (50) in the pre-tensioned position. After the insertion and the engagement of the, for example, prefilled cylinder/piston unit (100), the closure cap (120) is positioned. Finally, the originality closure (90) is fitted.

After the assembly, the layer (140) of the resiliently deformable material surrounds the lower region of the piston actuation ram (60), the intermediate space (141) and the upper region of the piston (111) and the cylinder (101) in a radial direction.

In order to prepare the single-use injector (4) for use, the banderole (90) and the closure cap (120) are first removed. After the single-use injector (4) has been placed on the skin of the patient, the end face (103) of the cylinder/piston unit (100) is located or adhesively bonded on the optionally tensioned skin with the outlet opening (106) in a planar manner.

For triggering, the triggering element (82) is displaced downward relative to the housing (100) in the illustration of FIGS. 8-10 in the triggering direction, that is to say, in the direction of the outlet opening (106). In this instance, the cams (22) of the support rods (21) slide upward relative to the triggering sleeve (82) along the inner wall (132). As soon as the expansion (83) reaches the cams (22), the cams (22) are abruptly displaced outward into this expansion (83) by means of the resilient energy store (50) and the ram plate (73). This unstable state is illustrated in FIG. 9.

The piston actuation ram (60) is now released and, under the action of the relaxing resilient energy store (50), moves rapidly forward, that is to say, in the triggering direction (6) in the direction of the cylinder/piston unit (100). In this instance, the piston sliding member (76) abruptly strikes the piston (111) of the piston/cylinder unit (100). In this instance, there are emitted sound waves which spread from the contact location of the piston sliding member (76) and the piston (111). They penetrate the gaps of the housing (10) which are located between the support rods (21) and strike the resiliently deformable material (140). Here, they are damped and do not reach the environment or reach the environment only to a small extent. The impact which occurs when the piston actuation ram (60) strikes the piston (111) can consequently hardly be heard by the patient. He does not become frightened and therefore does not recoil. The single-use injector (4) retains its position so that the active agent solution (1) can be introduced into the skin of the patient without loss.

With the further relaxation of the resilient energy store (50), the piston actuation ram (60) is displaced further forward and pushes the piston (111) further in the direction of the outlet opening (106). The medicament solution (1) is pushed out of the cylinder/piston unit (100) through the outlet opening (106), cf. FIG. 10.

The layer (140) of resiliently deformable material may also be arranged on the housing (10). It is thus conceivable to arrange this closed layer (140) on the inner side or on the outer side of the support rods (21). In this instance, the layer (140) may have beads or elevations so that the movement of the support rods (21) is not impeded.

After the injection, the single-use injector (4) can be disposed of. The single-use injector (4) illustrated here is constructed without any needle. However, it is also conceivable to construct a single-use injector (4) with a needle.

Figure 11:
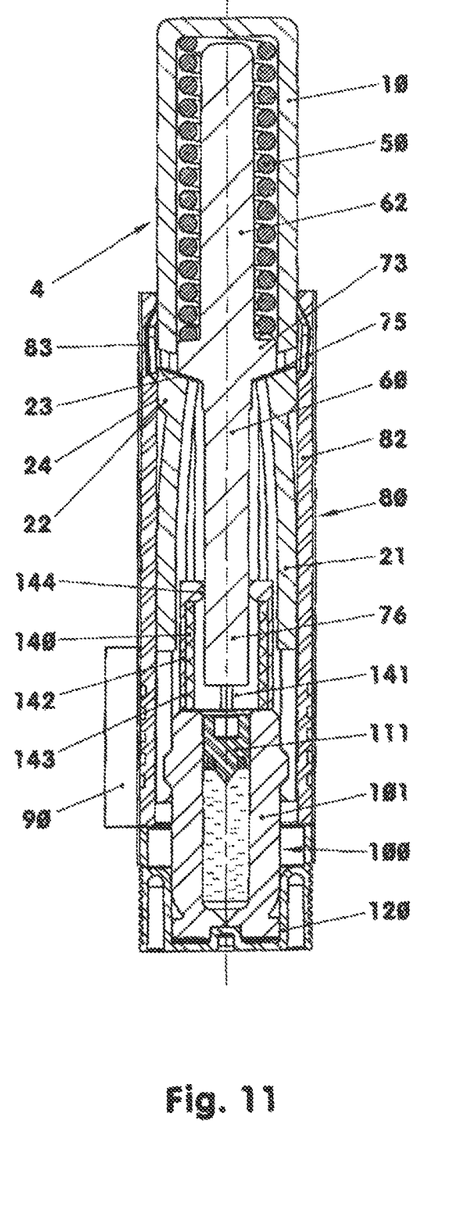
FIG. 11: shows a single-use injector with an inserted insulation sleeve.
Figure 12:
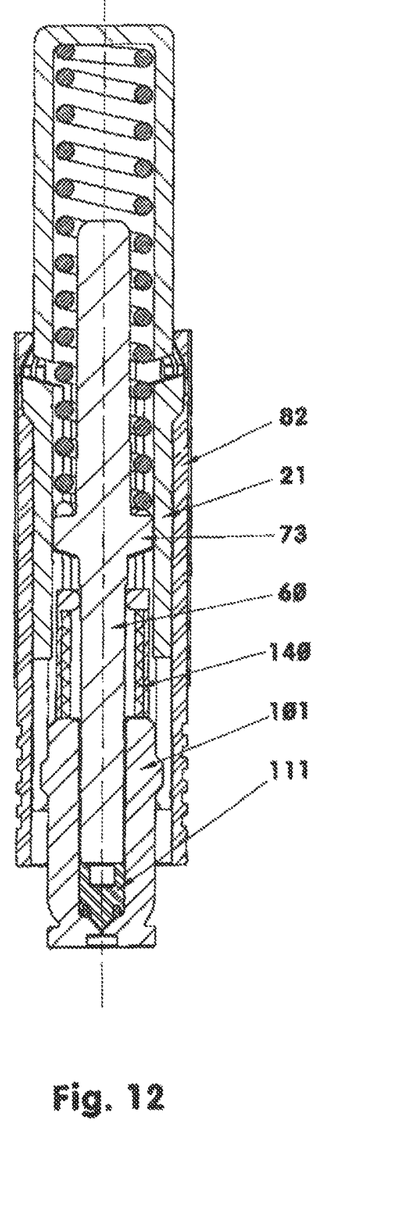
FIG. 12: shows a single-use injector from FIG. 11 with the piston pushed out.

FIGS. 11 and 12 show a single-use injector (4) which is constructed in a similar manner to the single-use injector (4) illustrated in FIGS. 8-10. On the piston sliding member (76) of the piston actuation ram (60) there is located an insertion sleeve (142). This sleeve surrounds in the initial state illustrated in FIG. 11 the front end of the piston sliding member (76) and protrudes forward, that is to say, beyond it in the triggering direction (6). In the embodiment illustrated, the insertion sleeve (142) is located on the cylinder/piston unit (100). The upper end of the piston (111) is located, for example, below the upper plane of the cylinder (101).

The insertion sleeve (142) comprises a carrier member (143) and a closed layer (140) of resiliently deformable material. The latter is directed inward. However, it is also conceivable to arrange the layer (140) on the covering face of the carrier member (143). With an upper inner ring (144), the insertion sleeve is in abutment in this embodiment with the piston sliding member (76) and is guided along the piston sliding member (76). Where which applicable, the piston sliding member (76) may have a waist portion in which the inner ring (144) engages during assembly. The inner ring (144) with the insertion sleeve (142) can then be displaced between the two ends of the waist portion.

The assembly is carried out substantially as described in connection with the second embodiment. After the piston actuation ram (76) has been inserted into the housing (10) and the helical compression spring (50) has been pretensioned, the insertion sleeve (142) is, for example, pushed onto the piston sliding member (76). It may, for example, be in abutment with the piston sliding member (76) in a frictionally engaging manner, engage in a waist portion, etcetera. It is also conceivable to fix the insertion sleeve (142) to the cylinder (101) of the cylinder/piston unit (100). For example, the insertion sleeve (142) may then be constructed to be self-supporting without abutment against the piston sliding member (76).

In this embodiment, the closure cap (120) is also positioned and the originality closure (90) is fitted after the insertion of the cylinder/piston unit (100).

The preparation of the triggering and the triggering are carried out as described in connection with the second embodiment. When the piston sliding member (76) strikes the piston (111), the dispersing sound waves are damped on the insulation layer (140). In the environment of the single-use injector (4), the impact can barely be heard. With an outer insulation layer, the carrier member (143) can direct the noise and reflect it by means of the inner wall thereof. However, the insulation layer surrounding the carrier member (142) prevents the noise from being discharged into the environment of the single-use injector (4). The dispensing of the injection solution (1) is carried out as described above. In FIG. 12, the emptied single use injector (4) is illustrated.

Figure 13:
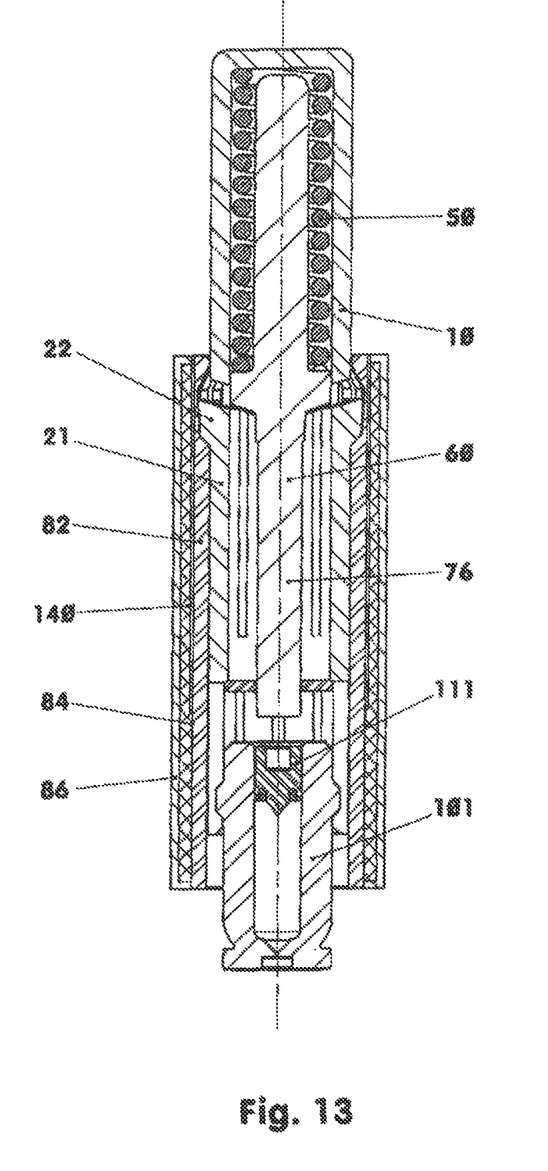
FIG. 13: shows a single-use injector with an external insulation layer.

FIG. 13 shows the single-use injector (4) with a triggering sleeve (82) on the outer covering face (84) of which the layer (140) of resiliently deformable material is arranged. This closed layer (140) engages round the piston actuation ram (60), the cylinder/piston unit (100) and the cams (22). The layer (140) consequently damps both the noise emissions which are produced when the cams (22) spring into the expansion (83) and the noises which are produced when the piston actuation ram (76) strikes the piston (111). In order to prevent a deformation of the noise insulation material (140) and consequently a reduction of the insulation effect by the user, an outer sleeve (86) surrounds the triggering sleeve (82) and the insulation material layer (140). It is also conceivable to construct the triggering sleeve as a double sleeve with two, for example, coaxial sleeves. The insulation material (140) is then arranged between the two sleeves.

Figure 14:
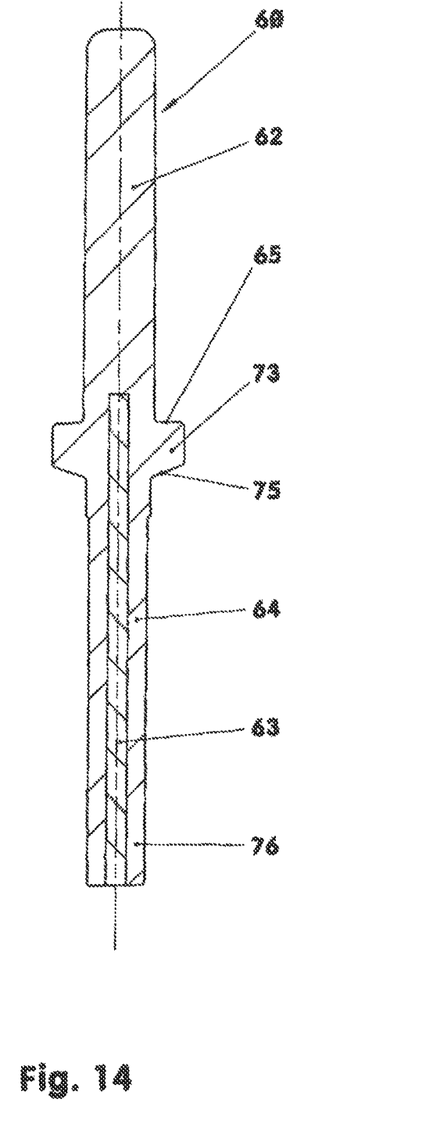
FIG. 14: shows a piston actuation ram of composite material.

FIG. 14 illustrates a piston actuation ram (60) which is produced from a composite material. The material of the cylindrical core (63) is, for example, an austenitic steel. The elasticity modulus thereof is, for example, 195,000 Newton per square millimeter. The material which surrounds the core (63) is in this embodiment a carbon-fiber-reinforced plastics material with an elasticity modulus of, for example, 70,000 Newton per square millimeter or less. The elasticity modulus of the core (63) is consequently at least twice as large as the elasticity modulus of the sheath (64) which surrounds the core (63) and which is, for example, vulcanized on. For the sheath (64), the use of a thermosetting or thermoplastic material is also conceivable.

The length of the core (63) in the longitudinal direction of the single-use injector (60) corresponds in this embodiment to the length of the piston sliding member (76) and the length of the ram plate (73). Where applicable, the core (63) may have a funnel-shaped or mushroom-shaped attachment. The upper end of the funnel then faces in the direction of the resilient support (65). The diameter of the cylindrical core (63) is in this instance, for example, a third of the diameter of the piston sliding member (76).

In the assembled single-use injector (4), there is further arranged around the piston sliding member (76) and the intermediate space (141) between the piston sliding member (76) and the piston (111) a closed layer (140) of a sound-insulation material.

When the piston sliding member (76) strikes the piston (111), the structure-borne noise spreads along the core (63). The structure-borne noise which is produced is damped by means of the sheath (64). The airborne noise which is produced during impact is damped by means of the closed layer (140) of the resiliently deformable material.

Of course, it is also conceivable to combine the different embodiments mentioned with each other. It is thus possible, for example, for a plurality of closed layers (140) of a resiliently deformable material to surround the contact location between the piston actuation ram (60) and the piston (111). These layers may, for example, be arranged concentrically with respect to each other. It is also conceivable to combine a sound insulation of the springing of the cams (22) and the airborne and structure-borne sound insulation of the impact of the piston actuation ram (60) on the piston (111).

LIST OF REFERENCE SIGNS

1 Injection solution
4 Single-use injector, disposable injector
5 Longitudinal direction
6 Triggering direction
7 Longitudinal center axis
10 Housing
11 Inner thread
12 Support Screw
13 Hexagonal portion
14 Flattened portion
15 Guiding rib
16 Housing opening, slot-like
17 Inner space
18 Housing opening with rectangular cross-section
19 Housing expansion
21 Support rods, locking rods
22 Cams
23 Support face
24 Abutment face
25 Clamping member
26 Wrap-around hook
27 Main member
38 Disk
39 Base
42 Resilient hook
50 Resilient energy store, helical compression spring, spring 60 Piston actuation ram
62 Guiding journal
63 Core
64 Sheath
65 Resilient support
66 Recesses
73 Ram plate
75 Collar face
76 Piston sliding member
77 Key flats
80 Triggering device, trigger unit
82 Triggering element, triggering sleeve
83 Expansion
84 Outer covering face
86 Outer sleeve
87 Securing sliding member, securing element
88 Outer wall
89 Gripping webs
90 Originality closure, banderole
100 Cylinder/piston unit
101 Cylinder
103 End face
106 Hole/discharge opening
111 Piston
120 Closure cap
122 Peripheral face
123 Fluting
131 Longitudinal ribs
132 Inner wall
133 Inner ring
134 Cylindrical portion
135 Carrying region
136 Recess
140 Layer of resiliently deformable material, layer material, insulation layer
141 Intermediate space
142 Insertion sleeve
143 Carrier member
144 Inner ring
145 Portion
146 Portion
147 Portion
151 Portion, one-piece
152-157 Portion, multi-piece
160 Support disk, pressure disk
161 Lower side
190 Triggering ring
191 Lower region
192 Cylindrical region
193 Inner wall
194 Rotation prevention groove
195 Abutment face
196 Metal insertion sheet, sliding plate
197 Shoulder
211 Retention ring
212 Assembly openings
220 Upper shell
221, 222 Reinforcement ribs, transverse ribs, one-piece
223-227 Reinforcement ribs, transverse ribs, two-piece
228 Journal
230 Lower shell
231 Reinforcement rib, transverse rib, one-piece
232-237 Reinforcement rib, transverse rib, two-piece
238 Journal holes
239 Longitudinal groove
241 Slot
250 Securing ring

What is claimed is:

1. A single use injector (4) having a housing (10), having a resiliently loaded piston actuation ram (60) which is arranged in the housing (10), the resiliently loaded piston actuation ram (60) having a cylindrical guiding journal (62), a ram plate (73) affixed to the cylindrical guiding journal (62) and a piston sliding member (76) affixed to the ram plate (73), the cylindrical guiding journal (62) configured to carry and guide a helical compression spring (50), the ram plate (73) is configured as a disk-like member and is oriented normally with respect to a longitudinal center axis (7) of the single use injector (4), the helical compression spring (50) at the bottom thereof contacts the ram plate (73) in an operative position, a trigger unit (80) is configured to unlock the resiliently loaded piston actuation ram (60), having a cylinder/piston unit (100) which comprises a cylinder (101) and a piston (111) which is spaced apart from the piston actuation ram (60), the piston sliding member (76) slidable within the cylinder (101) and adapted to strike the piston (111) within the cylinder (101) upon actuation of the piston actuation ram (60) and having means for damping at least one of structure-borne noise and airborne noise during triggering of the resiliently loaded piston actuation ram (60) for preventing recoil of a patient or other user during injection of the single use injector (4).

2. The single-use injector of claim 1, characterized in that the means for damping at least one of structure-borne noise and airborne noise during triggering of the resiliently loaded piston actuation ram (60) for preventing recoil of a patient or other user during injection of the single use injector (4) includes a closed noise insulation material layer (140) configured to surround the piston actuation ram (60) at least partially and protrudes therebeyond in a triggering direction (6).

3. The single-use injector (4) as claimed in claim 2, characterized in that the closed noise insulation material layer (140) comprises a resiliently deformable material.

4. The single-use injector (4) as claimed in claim 3, characterized in that the resiliently deformable material is an open-pore material.

5. The single-use injector (4) as claimed in claim 2, characterized in that the closed noise insulation material layer (140) is arranged on a carrier component (82; 143).

6. The single-use injector (4) as claimed in claim 5, characterized in that the thickness of the closed noise insulation material layer (140) corresponds to at least the thickness of a carrying region (135) of the carrier component (82; 143) which carries it.

7. The single-use injector (4) as claimed in claim 5, characterized in that the closed noise insulation material layer (140) is connected to the carrier component (82; 143) which carries it by a chemical or physical connection.

8. The single-use injector (4) as claimed in claim 2, characterized in that the triggering unit (80) comprises a tubular triggering element (82) which can be displaced in an axial direction relative to the housing (10).

9. The single-use injector (4) as claimed in claim 8, characterized in that the housing (10) and/or the triggering element (82) carries the closed noise insulation material layer (140).

10. The single-use injector (4) as claimed in claim 2, characterized in that the material of the closed noise insulation material layer (140) is a foam material.

11. The single-use injector (4) as claimed in claim 2, characterized in that the triggering of the piston actuation ram (60) is blocked by locking rods (21) having at least one wrap-around hook (26) or having triggering cams (22), wherein the closed noise insulation material layer (140) is arranged on the housing (10) and/or on the triggering element (82) and configured to surround at least the wrap-around hooks (26) or the triggering cams (22).

12. The single-use injector (4) as claimed in claim 2, characterized in that the piston actuation ram (60) comprises a composite material including a cylindrical core (63) comprising a first material and a sheath (64) comprising a second material configured to surround the cylindrical core (63), wherein the elasticity modulus of the first material of the cylindrical core (63) is at least twice as high as the elasticity modulus of the second material of the sheath (64) which surrounds the cylindrical core (63), whereby when the single-use injector (4) is triggered a structure-borne noise spread along the cylindrical core (63) is damped by the sheath (64).

* * * * *